United States Patent [19]
Wang et al.

[11] Patent Number: 5,814,741
[45] Date of Patent: *Sep. 29, 1998

[54] METAL SAMPLING METHOD AND SYSTEM FOR NON-HYDROLYZABLE GASES

[75] Inventors: Hwa-Chi Wang, Naperville; Richard J. Udischas, Chicago, both of Ill.

[73] Assignee: American Air Liquide Inc., Walnut Creek, Calif.

[ * ] Notice: The term of this patent shall not extend beyond the expiration date of Pat. No. 5,618,996.

[21] Appl. No.: 709,875

[22] Filed: Sep. 9, 1996

Related U.S. Application Data

[63] Continuation-in-part of Ser. No. 609,836, Mar. 1, 1996, Pat. No. 5,618,996.

[51] Int. Cl.$^6$ .................................................. G01N 1/22
[52] U.S. Cl. ............................................................ 73/863.12
[58] Field of Search ........................ 73/863.61, 863.23, 73/863.12

[56] References Cited

U.S. PATENT DOCUMENTS

| | | | |
|---|---|---|---|
| 2,322,018 | 6/1943 | Huber | 73/863.61 |
| 3,429,186 | 2/1969 | Price et al. | 73/863.61 |
| 4,004,882 | 1/1977 | Byrne et al. | 73/863.12 X |
| 4,317,379 | 3/1982 | Oberländer et al. | 73/863.12 |
| 4,979,403 | 12/1990 | Pike | 73/823.23 X |
| 5,142,143 | 8/1992 | Fite et al. | 73/863.12 X |
| 5,209,102 | 5/1993 | Wang et al. | 73/28.01 |
| 5,261,452 | 11/1993 | McAndrew et al. | 137/606 |
| 5,567,887 | 10/1996 | Schleismon et al. | 73/863.12 |
| 5,595,709 | 1/1997 | Klemp | 73/863.12 X |

*Primary Examiner*—Thomas P. Noland
*Attorney, Agent, or Firm*—Burns, Doane, Swecker & Mathis, L.L.P.

[57] ABSTRACT

Provided is a portable system useful for sampling both particulate and vapor phase metallic impurities from gases that cannot by hydrolyzed. The system comprises a valve for introducing and controlling the exhaust of the gas to be sampled from the system. The metallic impurities are entrapped on a filter, with one filter being operated at ambient temperature to remove particulate metallic impurities, and with another filter being operated at a temperature below ambient in order to remove vapor phase metallic impurities. In operating the system, the system is first back-filled to create a pressure equilibrium across the valve which introduces the gas to the first filter. The flow of gas through the entire sampling system is controlled by means of a critical orifice located between the filter and the valve for controlling exhaust of the gas from the system. The entire system is portable and allows for transport of the system with its filters to a laboratory in order to permit the most sophisticated and effective analysis of the metallic impurities in the filters under controlled laboratory conditions.

23 Claims, 2 Drawing Sheets

METAL SAMPLING METHOD AND SYSTEM FOR NON-HYDROLYZABLE GASES

CROSS REFERENCE TO RELATED APPLICATIONS

This application is a Continuation-in-Part of application Ser. No. 08/609,836 filed Mar. 1, 1996, and now U.S. Pat. No. 5,618,996.

BACKGROUND OF THE INVENTION

1. Field of the Invention

The present invent ion relates to a method and a system for sampling a gas for both particulate and vapor phase metal impurities. In particular, the system of the present invention is very portable in that it can be easily removed from the site of the g as being sampled and returned to a laboratory for an accurate analysis of the metal impurities trapped in the filters of the system.

2. Brief Description of the Prior Art

A very important and crucial aspect in semiconductor manufacturing is the constant control of metallic impurities in process gases. Such metallic impurities can exist in the vapor phase at room temperature and atmospheric pressure up to very high concentrations, for example, up to 100 ppm. Such levels can be detrimental to the semiconductor devices formed.

Generally, the impurities are present due to corrosion, shedding from valves and the like. In order to reduce the metallic impurities in the gases prior to their reaching the semiconductor manufacturing process, the gases flowing through the system must be sampled. Analysis of the gases can indicate whether metallic impurities, being introduced from outside the system or being created inside the system, are contaminating the manufacturing process. The level of detection for metallic impurities in semiconductor manufacturing processes must reach the parts per trillion level, and therefore requires very sophisticated equipment for analysis and detection.

Methods for sampling gases in order to detect metallic impurities have applications well beyond the semiconductor manufacturing industry. In most of the methods used, the gases are hydrolyzable, i.e., dissolvable in water, and therefore hydrolysis is commonly used for sampling the metals in the gases. However, gases such as nitrogen ($N_2$), silane ($SiH_4$), and tetrafluoromethane ($CF_4$), some of which are commonly used in semiconductor manufacturing processes, are not hydrolyzable. Therefore, in order to sample the gases and detect metal impurities in such gases, a filtering system must be used.

To render such a filtering system most useful for the industry, it must be very efficient and effective for measuring and detecting metallic impurities to the parts per trillion level. Efficiency in such detection often requires the most sophisticated of analysis equipment, and therefore it would also be most desirable if such a filtering system were portable so that it can be easily transported to a laboratory where access to the necessary analysis equipment can be had.

Accordingly, it is an object of the present invention to provide a sampling system and method for using such a system to sample non-hydrolyzable gases and to analyze the gases for metal impurities.

It is another object of the present invention to provide methods and systems to sample non-hydrolyzable gases for both particulate and vapor phase metallic impurities in an effective and efficient manner.

It is yet another object of the present invention to provide a portable system for sampling non-hydrolyzable gases for the ultimate detection of metallic impurities so that the sophisticated analysis equipment typically required can be easily used at an off-site laboratory.

These and other objects of the present invention will become apparent upon a review of the following specification, the figure of the Drawing, and the claims appended hereto.

SUMMARY OF THE INVENTION

In accordance with the invention, a portable system useful for sampling both particulate and vapor phase metallic impurities from gases that cannot be hydrolyzed is presented, as well as a method of using same.

The system preferably comprises a first valve means for introducing the gas to be sampled to the system. A first filter means is located downstream of the first valve means, which first filter means is used to remove particulate metallic impurities, preferably at ambient temperature (about 20°–25° C.). A second filter means in series with the first filter means is used to remove vapor phase metallic impurities. This second filter means is preferably operated at a temperature below ambient temperature but above the freezing point of the gas being sampled. A third filter means is also located downstream of the first and second filter means for removing substantially any impurities in the gas. The system further comprises a second valve means downstream from the first valve means but upstream from the first filter means. Third and fourth valve means are also included in the system, with the fourth valve means being located downstream of all of the filter means and is used for controlling the exhaust of the gas from the system. The third valve means allows for the gas to be conducted in parallel with respect to the filters in the system to the fourth valve means. A critical orifice is also located between the third filter means and the fourth valve means for back-filling the gas being sampled through the filters in the system until there is a pressure equilibrium across the second valve means for reasons that will become apparent.

The system of the invention is most preferably portable and can be transported quite easily, generally using a system pressure of less than 20 npsig. Due to the portability of the inventive system, the filters can be transported to a laboratory which can analyze the filters for particulate and vapor phase metallic impurities.

A preferred method of using the system comprises first opening the first and third valve means, while keeping the second and fourth valve means closed. This allows the gas being sampled to back-fill through the critical orifice and the third filter means, which is an absolute filter to ensure that the system is filled first with only clean (i.e., metal impurity-free) gas. This back-filling allows a pressure equilibrium to be established across the second valve means. This pressure equilibrium is important as it substantially reduces, and preferably prevents particle shedding from the second valve when it is opened. After the back-filling is complete, the third valve means is closed, and the second and fourth valve means are opened to allow sampling to begin. Metallic impurities are trapped in the first and second filter means. After the necessary sampling duration, the first and fourth valve means are closed in order to close the entire system. The system can then be disconnected from the customer's process and sent to a laboratory for analysis of the filters.

BRIEF DESCRIPTION OF THE DRAWINGS

The objects and advantages of the invention will become apparent from the following detailed description of the preferred embodiments thereof in connection with the accompanying drawings, in which.

DESCRIPTION OF PREFERRED EMBODIMENTS

The system of the present invention is preferably portable and allows for the efficient and effective sampling of gases which are non-hydrolyzable in order to determine the extent of any metallic impurities in said gases. As used herein, portable means the system can be disconnected from the gas supply being sampled and sent to the location of the analysis equipment. The location of analysis equipment may be removed from the sampling site, or on-site. The portability of the present system allows its use in many different locations, yet further allows analysis of the gases sampled to be conducted with the most sophisticated equipment possible in the most efficient and effective manner.

Figure 1:
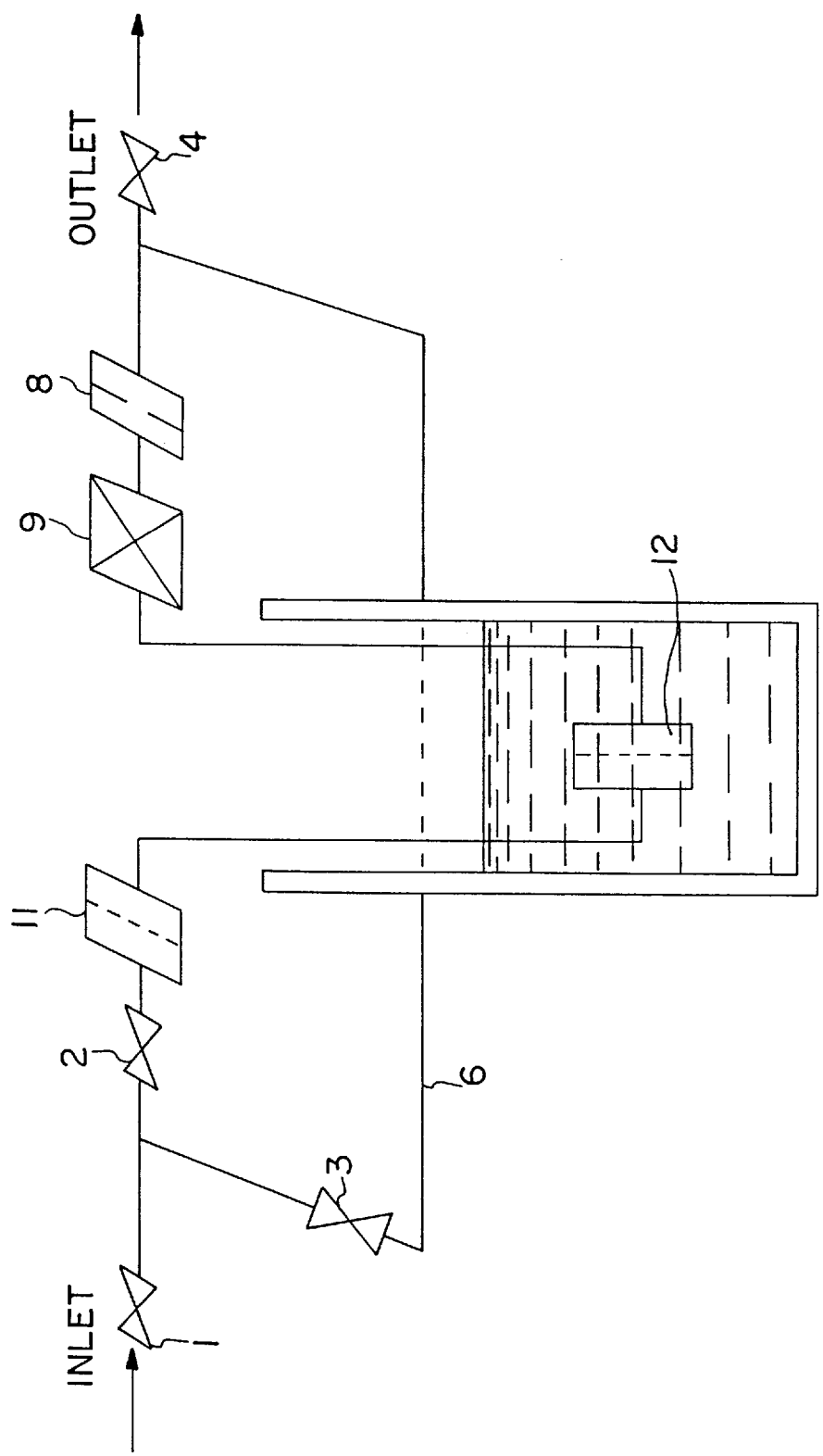
FIG. 1 is a schematic representation (reduced in scale) of a system in accordance with the present invention, and is illustrative only.

The system and the method used in sampling gases with the system will be described in more detail in reference to FIG. 1. As shown in FIG. 1, a first valve means 1 is generally connected to the system from which the gas is to be sampled. The connection may be any type of connection means commonly used in gas systems. First valve means 1 allows the gas to be sampled to be introduced into the sampling system illustrated. A fourth valve means 4 of the sampling system controls the exhaust of the gas from the system.

A second valve means 2 of the system is located downstream from first valve means 1 but upstream from a first filter 11. First filter means 11 is used to remove particulate impurities at ambient temperature. The filter is generally and preferably a membrane filter and has an effective pore size of about 0.2 micrometer. Membrane filter 11 can be any appropriate membrane filter, but is most preferably a teflon membrane filter, such as those commercially available. In series with filter means 11 is filter means 12. Filter means 12 is generally composed of the same media as filter means 11, but can be maintained at a lower than ambient temperature, and at a temperature greater than the freezing point of the gas being sampled. This lower than ambient temperature is utilized in order to have vaporous metal impurities nucleate or condense onto the membrane filter.

Figure 2:
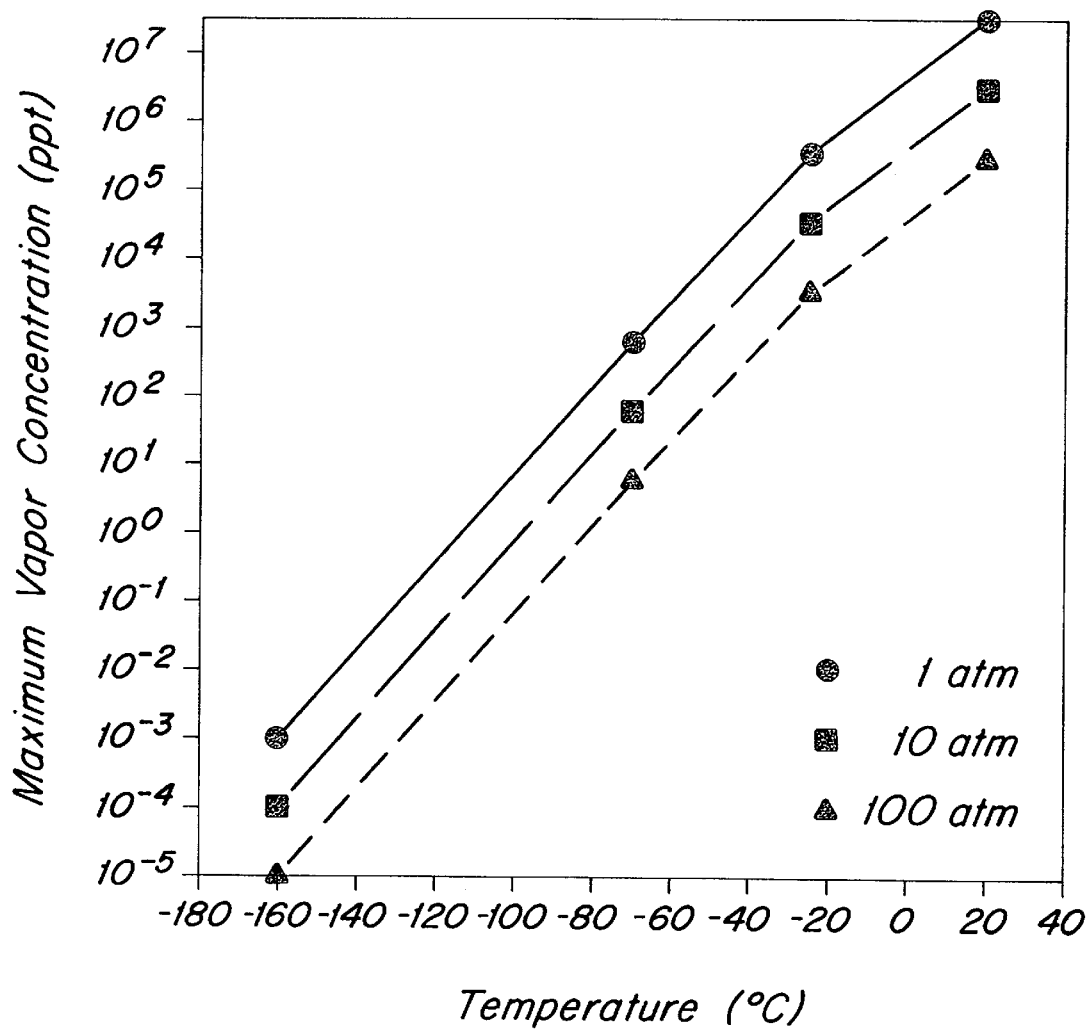
FIG. 2 is a graph that depicts the maximum vapor concentration of $AlBr_3$ as a function of temperature at various pressures.

In particular, the temperature of filter means 12 is variable, and is selected dependent upon the particular vaporous metal impurity to be measured. More specifically, the desired temperature of filter means 12 will depend on the vapor pressure of the metallic impurity to be measured. A sample vapor concentration curve is provided in FIG. 2, which illustrates maximum vapor concentration as a function of temperature for $AlBr_3$ for pressures of 1, 10 and 100 atmospheres. As can be seen in FIG. 2, maximum vapor concentration increases with increased temperature. Conversely, the maximum vapor concentration decreases with increases in pressure.

From vapor pressure, the maximum allowable concentration of vapor which can exist at a given pressure can be determined. In the event the metallic compound is present at a concentration in excess of the maximum allowable concentration, the metal vapor will condense, thereby forming a solid which is trapped on filter means 12. For example, the vapor pressure of $AlBr_3$ at 20° C. and a pressure of one atmosphere (ambient conditions) is 0.0198 torr. This corresponds to an $AlBr_3$ concentration of 26 ppm (0.0198 torr/760 torr).

The sensitivity of the system for various metal impurities at atmospheric pressure for several temperatures has similarly been determined, and is shown in the table below.

| Maximum Vapor concentration of Various Metals at 1 atm | | | | |
|---|---|---|---|---|
| Compound | 20° C. | −25° C. | −70° C. | −160° C. |
| Ag | <1 ppq[1] | <1 ppq | <1 ppq | <1 ppq |
| $AlBr_3$ | 26 ppm[2] | 350 ppb[3] | 628 ppt[4] | <1 ppq |
| $AlCl_3$ | 46 ppb | 9 ppt | <1 ppq | <1 ppq |
| $AsBr_3$ | >100 ppm | 10 ppm | 56 ppb | <1 ppq |
| $AsCl_3$ | >100 ppm | >100 ppm | 6 ppm | 25 ppq |
| $AsF_3$ | >100 ppm | >100 ppm | >100 ppm | 5 ppt |
| $BBr_3$ | >100 ppm | >100 ppm | >100 ppm | 8 ppt |
| $BCl_3$ | >100 ppm | >100 ppm | >100 ppm | 24 ppb |
| $CR(CO)_6$ | >100 ppm | >100 ppm | 4 ppb | <1 ppq |
| $CrO_2Cl_2$ | >100 ppm | >100 ppm | 11 ppm | 62 ppq |
| $Cu_2Br_2$ | 8 ppq | <1 ppq | <1 ppq | <1 ppq |
| $CuCl_2$ | 300 ppq | <1 ppq | <1 ppq | <1 ppq |
| K | 17 ppt | 28 ppq | <1 ppq | <1 ppq |
| Li | <1 ppq | <1 ppq | <1 ppq | <1 ppq |
| $Ni(CO)_4$ | >100 ppm | >100 ppm | >100 ppm | 3 ppb |
| $HgBr_2$ | 290 ppb | 1 ppb | 523 ppq | <1 ppq |
| $HgCl_2$ | 140 ppb | 436 ppt | 83 ppq | <1 ppq |
| $NiCl_2$ | <1 ppq | <1 ppq | <1 ppq | <1 ppq |
| $SiCl_4$ | >100 ppm | >100 ppm | >100 ppm | 250 ppt |
| $SiF_4$ | >100 ppm | >100 ppm | >100 ppm | 47 ppm |
| Na | 22 ppq | <1 ppq | <1 ppq | <1 ppq |
| $SnBr_4$ | >100 ppm | >100 ppm | 211 ppb | <1 ppq |
| $SnCl_4$ | >100 ppm | >100 ppm | 17 ppm | 165 ppq |
| $ZrBr_4$ | 26 ppt | 5 ppq | <1 ppq | <1 ppq |
| $ZrCl_4$ | 79 ppt | 25 ppq | <1 ppq | <1 ppq |

[1] parts per quintillion (ppq)
[2] parts per million (ppm)
[3] parts per billion (ppb)
[4] parts per trillion (ppt)

In practice, sensitivity of the system can be increased considerably over the levels shown in the above table, since the sampling can be performed at pressures in excess of atmospheric pressure. Thus, a suitable sampling pressure can be selected based on the concentration level of interest for a given impurity. The sampling pressure often corresponds to the pressure of the gas in the distribution system. For example, in the case of a typical house nitrogen supply, the sampling pressure is generally about 20 psig. However, higher pressures of, for example, up to 3000 psig can be used.

The filter can be maintained at temperatures in the range of from about −170° C. to 0° C., depending on the metallic impurity of interest. Temperatures in the range of −80° C. to 0° C. are preferred. Liquid nitrogen can be used for cooling filter means 12 to a temperature in the range of from about −170° C. to −160° C. For higher temperatures in the range of from about −80° C. to −60° C., dry ice together with a suitable liquid can be used. The liquid functions primarily to increase the contact area of the bath with the filter to ensure uniform temperature. In a preferred embodiment, a carbon dioxide ice/methanol liquid bath can be used to maintain the temperature of filter 12 at about −60° C. Other combinations of coolants and temperature baths can be used in order to vary the temperature of second filter means 12. Ice water can be used to attain a temperature of about 0° C., while a temperature controlled water bath can be used for higher temperatures.

An important aspect of the present system is that it allows back-filling of the system with clean gas to create an equal pressure on both sides of second valve means 2. This pressure equilibrium allows one to avoid particle shedding when valve means 2 is opened. Shedding is basically a mechanical friction and corrosion problem. It involves the release of particles from internal wetted surfaces, i.e., anything the gas comes into contact with in the system. The release of the particles is caused generally by pressure pulses or flow pulses, which provide the energy to pull the particle into the gas.

The back-filling is accomplished by use of a conduit 6 which is in parallel flow arrangement with the filters in the system. Gas flowing through conduit 6 is controlled by a third valve means 3 in the system. When valve means 3 is open, gas will flow parallel to the filters in the system directly to valve means 4, where it will be exhausted from the system when valve means 4 is open. However, when valve means 4 is closed, the gas conducted via means of conduit 6 will back-fill through the filters in the system. The back-filling takes place through an orifice 8 and absolute filter 9. Orifice 8 is preferably a critical orifice, and is used to control the flow of gas through the system. The critical orifice can be stainless steel disk, for example, with one hole which is sized to correspond to the pressure one plans on working with in the system. The hole is sized appropriately based on the desired pressure in order to give the desired flow rate. The orifice can be made out of sapphire or other suitable materials besides stainless steel.

The absolute filter 9 is generally a ceramic or metal filter which removes substantially all impurities which may be contained in the gas to be sampled. The filter is preferably a ceramic filter which has a rating of 0.01 micrometer or lower. The use of this filter ensures that clean gas is back-filled through the system.

The amount of time that back-filling takes place generally ranges from about one—two minutes. Of course, critical orifice 8 controls the flow, and therefore the choice of the critical orifice size can control the amount of time it would take to back-fill the entire system. In general, however, about two minutes is all that is necessary to slowly fill the system and create the same pressure on both sides of second valve means 2. Once the system has been back-filled, sampling of the gas through the system can take place, with particulate impurities being entrapped in filter means 11 and vapor phase metallic impurities being entrapped in filter means 12.

Once sampling has been completed, the system is closed, generally by closing valve means 1 and 4. The closed system is then disconnected from the customer's facility and, due to its portability, then can be simply transported from the system from which the sampled gas has been taken to the analysis location. For example, the portable system is preferably transported to a laboratory where analysis of the filters can take place in order to indicate the extent of metal impurities in the sampled gas. Generally, an acid solution, preferably a mixture of nitric acid and hydrochloric acid, is used to remove the metals from filters 11 and 12. This acid solution containing the metal impurities is then injected into an instrument such as ICP-MS (Inductively Coupled Plasma Mass Spectrometer) or a GFAA (Graphite Furnace Atomic Absorption) instrument. Both of these types of instruments are extremely sophisticated, but the operation of the instruments is known to skilled artisans and the instruments are commercially available, for example from Perkin-Elmer.

Of particular utility of the present portable system is the ability to entrap vapor metal impurities. In addition to the impurities set forth in the table above, other examples of impurities which can be entrapped include aluminum, copper, zinc, iron, chromium, cobalt, manganese or magnesium, as well as molybdenum. The aluminum can often be generated from aluminum oxide used in adsorbents. Even small quantities in parts per trillion of such metals can do damage in very sensitive processes such as semiconductor manufacturing processes. Thus, detection of such metals, particularly in the vapor phase, would allow a re-evaluation of the manufacturing process, and would permit one to detect leaks and/or sources of the impurities more conveniently by moving the sample system from sample port to sample port.

A calculation of the concentration of metals in the gas can be made by continuously monitoring the pressure across first filter means 11 in the system. The measurement of the pressure can be monitored by a transducer on a continuous basis with the data being fed into a computer. Orifice 8 and its size together with the pressure information can be used to calculate the mass of gas sampled. The metals analysis can provide the mass of the metal. Therefore, using the mass of the gas and metal allows one to calculate the concentration of the metals in the gas sampled. It is often important to continuously monitor the pressure across the first filter means 11 because the pressure in many plants or systems can vary quite a bit over time. Thus, continuous monitoring of the pressure is often necessary for an accurate calculation.

Referring to FIG. 1, once again, a method of utilizing the system for sampling the gas and detecting metallic impurities therein will be described in more detail. First, the system is connected to the desired sample point, with all valves of the system closed. Prior to beginning sampling, valves 1 and 3 are opened so that pressure can be equalized on both sides of valve means 2. In opening valves 1 and 3, the gas is allowed into the system and the sampled gas back-fills the system through the various filters. The back-fill of the gas goes through orifice 8 and absolute filter 9, as well as filters 12 and 11. After pressure has been equalized on both sides of valve means 2, which generally takes about one to three minutes, valve means 3 is closed, and valve means 2 and 4 are opened. Preferably, valve means 4 is opened slowly in order to ensure there are no pressure fluctuations throughout the system. Once the necessary sampling has been completed, the pressure is reduced to a predetermined safe level for transport, and then valve means 1 and 4 are closed in order to close down the system. To prevent vaporization and loss of material accumulated on filter means 12 during transport of the sampling system, the temperature of filter means 12 should be maintained at substantially the same temperature during sampling and transport.

While the invention has been described with preferred embodiments, it is to be understood that variations and modifications may be resorted to as will be apparent to those skilled in the art. Such variation and modifications are to be considered within the purview and the scope of the claims appended hereto.

What is claimed is:

1. A system useful for sampling impurities, which system comprises:

a sample conduit connected to receive a flow of a gas, and a parallel conduit connected to said sample conduit at first and second locations, the second location being downstream of the first location;

first valve means downstream of the second location through which gas is exhausted from the sampling system;

first and second filter means in said sample conduit, which second filter means is operated at a temperature below ambient temperature;

second valve means upstream of the first and second filter means but downstream of the first location;

third valve means in said parallel conduit, for allowing gas to be conducted in parallel with respect to the first and second filter means of the system to allow back-filling of the gas through the first and second filters in the system until pressure on both sides of the second valve means is equalized.

2. The system of claim 1, wherein the temperature of the second filter means is variably controllable.

3. The system of claim 1, wherein the second filter means is maintained at a temperature in the range of from about −170° C. to 0° C.

4. The system of claim 3, wherein the second filter means is maintained at said temperature by use of liquid nitrogen.

5. The system of claim 3, wherein the second filter means is maintained at said temperature by use of a dry ice/methanol liquid bath.

6. The system of claim 1, wherein the first and second filter means are membrane filters.

7. The system of claim 6, wherein the membrane filters of the first and second filter means are polytetrafluoroethylene membrane filters.

8. The system of claim 7, wherein the polytetrafluoroethylene membrane filters have a pore size of 0.2 micrometer.

9. The system of claim 1, further comprising a third filter downstream of said first and second filters.

10. The system of claim 9, wherein said third filter is a ceramic filter rated at 0.01 micrometer or less.

11. The system of claim 1, wherein said first, second and third valve means are stainless steel high-pressure diaphragm valves.

12. The system of claim 1, wherein the system is portable.

13. A method for sampling a gas for impurities using the apparatus of claim 1, which comprises first opening of the third valve means while keeping the first and second valve means of the system closed, thereby allowing the gas to back-fill through the first and second filter means of the system in order to create a pressure equilibrium on both sides of the second valve means, closing the third valve once the back-filling is complete and opening the first and second valve means to allow sampling to occur by means of trapping impurities in the first and second filter means.

14. The method of claim 13, wherein the method further comprises removing the entire supply system from the system to which it is connected and from which the gas has been sampled, and transporting the sampling system to a laboratory for analysis of impurities of the first and second filters.

15. The method of claim 14, wherein the impurities are metallic impurities which cannot be hydrolyzed.

16. The method of claim 14, wherein the analysis of the first and second filters is conducted using an inductively coupled plasma mass spectrometer or a graphite furnace atomic absorption instrument.

17. The method of claim 14, wherein the pressure of the system is less than 20 psig.

18. The method of claim 13, wherein the pressure across the first filter means is monitored continuously.

19. The method of claim 13, wherein the second filter means is operated at a temperature in the range of from −170° C. to 0° C.

20. The method of claim 19, wherein liquid nitrogen is used to maintain the temperature of the second filter means.

21. The method of claim 19, wherein a dry ice/methanol liquid bath is used to maintain the temperature of the second filter means.

22. The method of claim 13, wherein the first and second filter means are membrane filters.

23. The method of claim 13, wherein the first and second valve means are stainless steel high-pressure diaphragm valves.

* * * * *